(12) United States Patent
Yoon et al.

(10) Patent No.: US 8,012,093 B2
(45) Date of Patent: Sep. 6, 2011

(54) ULTRA SOUND SYSTEM FOR FORMING STRAIN IMAGES WITH INSTANTANEOUS FREQUENCY

(75) Inventors: Ra Young Yoon, Seoul (KR); Sung Jae Kwon, Seoul (KR); Moo Ho Bae, Seoul (KR); Mok Kun Jeong, Seoul (KR)

(73) Assignee: Medison Co., Ltd., Hongchun-gun (KR)

( * ) Notice: Subject to any disclaimer, the term of this patent is extended or adjusted under 35 U.S.C. 154(b) by 61 days.

(21) Appl. No.: 12/495,210

(22) Filed: Jun. 30, 2009

(65) Prior Publication Data

US 2009/0318811 A1    Dec. 24, 2009

Related U.S. Application Data

(63) Continuation-in-part of application No. 11/434,890, filed on May 17, 2006, now abandoned.

(30) Foreign Application Priority Data

Jul. 27, 2005   (KR) .................. 10-2005-0068251
Nov. 16, 2005   (KR) .................. 10-2005-0109477

(51) Int. Cl.
*A61B 5/103*   (2006.01)
*A61B 8/00*    (2006.01)
*G01B 7/16*    (2006.01)

(52) U.S. Cl. ........ 600/442; 600/587; 600/504; 600/437; 600/443; 600/463; 73/763; 324/309

(58) Field of Classification Search .................. 600/449, 600/438, 442, 504; 382/128; 73/625, 723
See application file for complete search history.

(56) References Cited

U.S. PATENT DOCUMENTS

| 6,132,380 A | 10/2000 | Cohen et al. | |
| 7,223,241 B2* | 5/2007 | Radulescu | 600/443 |
| 2002/0040187 A1* | 4/2002 | Alam et al. | 600/442 |
| 2006/0084870 A1 | 4/2006 | Kim et al. | |
| 2007/0038090 A1 | 2/2007 | Moon et al. | |
| 2007/0167773 A1 | 7/2007 | Jeong et al. | |
| 2007/0167774 A1 | 7/2007 | Jeong et al. | |
| 2007/0197915 A1 | 8/2007 | Jeong et al. | |

FOREIGN PATENT DOCUMENTS

| JP | 2002-10399 | 1/2002 |
| JP | 2004-57652 | 2/2004 |

* cited by examiner

*Primary Examiner* — Unsu Jung
*Assistant Examiner* — Helene Bor
(74) *Attorney, Agent, or Firm* — Oblon, Spivak, McClelland, Maier & Neustadt, L.L.P.

(57) ABSTRACT

There is provided an ultrasound system for forming strain images by decreasing decorrelation of receive signals, which vary with time or space. More specifically, the decorrelation between the receive signals obtained without and with applying stress to a target object is reduced to decrease an error, which occurs during the calculation of a delay. Also, a center frequency, which varies with depth of a target object, is compensated to form the strain image.

6 Claims, 5 Drawing Sheets

ULTRA SOUND SYSTEM FOR FORMING STRAIN IMAGES WITH INSTANTANEOUS FREQUENCY

This is a continuation-in-part application of a prior U.S. patent application filed on May 17, 2006 (Ser. No. 11/434,890), which claims priority from Korean Patent Application Nos. 10-2005-68251 and 10-2005-109477 filed on Jul. 27, 2005 and Nov. 16, 2005, respectively.

FIELD OF THE INVENTION

Embodiments of the present invention may relate to an ultrasound system for forming strain images in an ultrasound imaging system, and more particularly to an ultrasound system for forming strain images by decreasing the decorrelation of ultrasound receive signals.

BACKGROUND OF THE INVENTION

An ultrasound imaging system is a device that is widely used in a medical field. In the ultrasound imaging system, ultrasound signals are transmitted to tissues in a target object like a human body, and the ultrasound signals reflected from the tissues are transformed to receive signals. An ultrasound image is formed with these receive signals.

The ultrasound image is mainly expressed with a brightness-mode (B-mode) based on reflection coefficients which vary with impedance differences between the tissues in the target object. However, it is hard to observe a lesion, such as a tumor or a carcinoma, with the B-mode image, because the reflection coefficients of the tumor or the carcinoma are not so much different from those of other tissues adjacent thereto.

Meanwhile, eleastrography for forming ultrasound elasticity images, i.e., strain images, utilizes mechanical characteristics of the tissues, which are difficult to be observed in the B-mode image, and thus the eleastrography can be a great assistance for the diagnosis of the lesion.

The mechanical characteristics of the tissues can be obtained by comparing a first receive signal and a second receive signal which are respectively obtained without and with applying stress, i.e., a force per a unit area, to the target object. The first and the second receive signals have a RF form.

Due to the stress, each tissue has different displacement, which reflects the mechanical characteristics, for example, hardness of the tissue. The displacement can be obtained in consideration of a phase difference or a delay between the first and the second receive signals. In the elastography, the displacement of each tissue can be obtained by computing a cross correlation or an autocorrelation of the first and the second receive signals. In the cross correlation, the first and the second receive signals in the RF form are computed. However, in the autocorrelation, the first and the second receive signals should be converted into I/Q baseband signals.

The autocorrelation has an advantage of enhancing speed of the computation because the data amount of the I/Q baseband signals is less than that of the RF signals. However, the autocorrelation expresses the displacement in terms of a phase value, and thus an additional step is required to convert the phase value into a time value.

A center frequency of ultrasound transmission signals is used to convert the phase value into the time value. The center frequency varies with the depth of the tissue in the target object, and consequently an error will arise if a fixed value is used as the center frequency during the conversion of the values.

In case that the phase value is computed by using the autocorrelation, aliasing is generated when the phase difference of first and the second receive signal is greater than ½ wavelength of the ultrasound transmission signals. Therefore, an additional process should be introduced to compensate for the aliasing.

As the depth of the tissue becomes deeper, the first and the second receive signals are increasingly different in phase and shape, and thus error also increases due to the decorrelation of the first and the second receive signals.

BRIEF DESCRIPTION OF THE DRAWINGS

The above and other objects and features in accordance with the present invention will become apparent from the following descriptions of preferred embodiments given in conjunction with the accompanying drawings, in which.

DETAILED DESCRIPTION OF THE PRESENT INVENTION

Hereinafter, the embodiments of the present invention will be described by referring to the attached drawings.

A first receive signal in an RF form is obtained by transmitting ultrasound signals from a probe to a target object without applying stress to tissues in the target object. A second receive signal, also in the RF form, is obtained with applying the stress to the tissues. Along the direction of the stress, the tissues in the target object move, so that the second receive signal is delayed, comparing with the first receive signal.

If the center frequency and amplitude of the transmitting ultrasound signal are denoted as $\omega_0$ and $r(t)$, respectively, the first receive signal and the second receive signal having the RF form can be defined as $x_1(t)$ and $x_2(t)$ as shown in equations 1 and 2, respectively.

$$x_1(t) = r(t)\cos(\omega_0 t + \phi(t)) \quad \text{(Equation 1)}$$

$$x_2(t) = r(t-\tau)\cos(\omega_0(t-\tau) + \Phi(t-\tau)) \quad \text{(Equation 2)}$$

Figure 1:
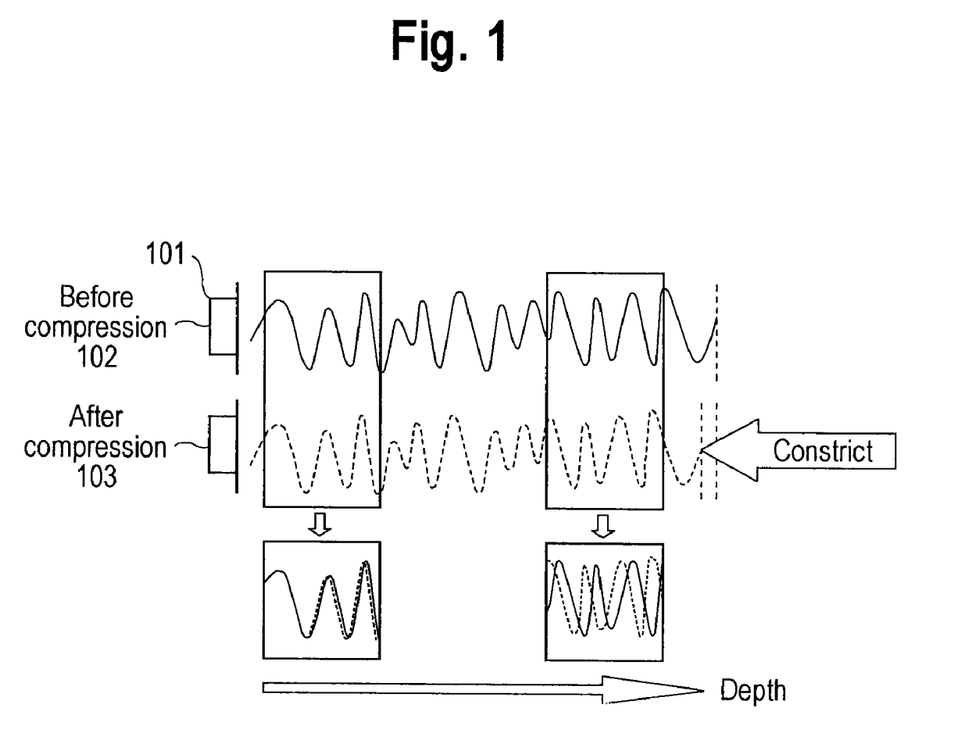
FIG. 1 shows a graph of a first and a second receive signals obtained without and with applying stress to a target object, respectively.
Figure 2:
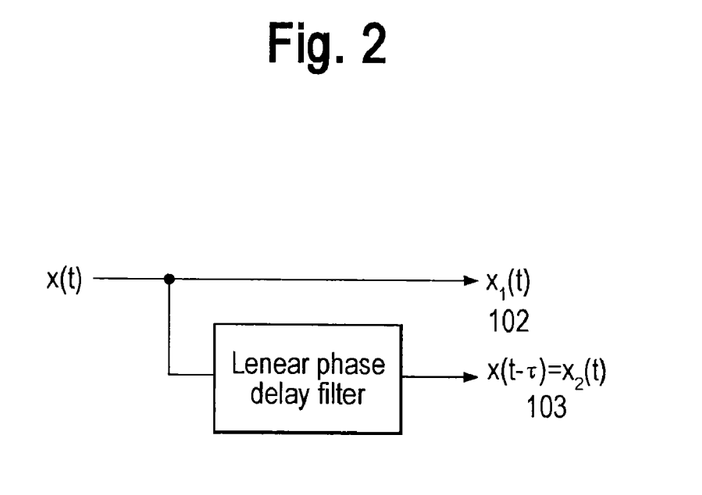
FIG. 2 is a schematic diagram of a delay signal model for computing a delay.

In equations 1 and 2, '$\phi(t)$' denotes phase which varies with time, and '$\tau$' denotes the delay due to the stress. FIG. 1 shows shapes of the first and the second receive signals. As shown in FIG. 2, the delay $\tau$ due to the stress is modeled with an all pass filter having a linear delay.

The delay of the second receive signal is smaller at a region near the probe than other regions far from the probe, because the phase difference of the first and the second receive near the probe is relatively small.

A displacement of each tissue can be calculated with the delay of the second receive signal. The degree of the displacement of the tissue depends on hardness of the tissues when constant stress is applied to the tissues in one direction. Accordingly, a distortion ratio, i.e., strain can be obtained by calculating the displacement varied with the stress and by obtaining derivative of displacement between the first receive signal and the second receive signal. The elasticity ultrasound image, i.e., the strain image, is formed on the basis of the strain.

In order to calculate the correlation of the first and second receive signals with autocorrelation, the first and the second receive signals in the RF form are demodulated and converted into I/Q baseband signals, and the delay is computed to obtain the phase difference of the first and second receive signals. By demodulating, the first and the second receive signals can be converted into I/Q baseband signals as below equations 3 and 4.

$$x_1(t) = r(t)e^{j\phi(t)} \quad \text{(Equation 3)}$$

$$x_2(t) = r(t-\tau)e^{j(-\omega_0\tau + \phi(t-\tau))} \quad \text{(Equation 4)}$$

Phase difference $\Delta\phi$ between the first and the second receive signals can be obtained by computing the correlation of the first receive signal $x_1(t)$ and second receive signal $x_2(t)$ as expressed in equation 5.

$$\Delta\Phi = \arg\langle x_1 \cdot x_2^* \rangle = \omega_0\tau + \phi(t) - \phi(t-\tau) \quad \text{(Equation 5)}$$

In the equation 5, "$\langle \cdot \rangle$" denotes a function for computing the correlation operation and "arg$\langle \cdot \rangle$" denotes a function for obtaining the phase. The first term of the Taylor series expansion of $\phi(t-\phi)$ is expressed as below equation 6.

$$\phi(t-\tau) \approx \phi(t) - \tau\phi'(t) \quad \text{(Equation 6)}$$

By applying the equation 6 to the equation 5, the phase difference $\Delta\Phi$ can be approximated as equation 7.

$$\Delta\Phi = \omega_0\tau + \tau\phi'(t) \quad \text{(Equation 7)}$$

The following equation 8 is obtained by rearranging the equation 7 with respect to the delay $\tau$.

$$\tau = \frac{\Delta\Phi}{\omega_0 + \phi'(t)} = \frac{\Delta\Phi}{\omega_0 + \omega_B(t)} \quad \text{(Equation 8)}$$

In question 8, '$\phi'(t)$' denotes a derivative of the phase, which can be considered as the instantaneous frequency $\omega_B$ of the first or the second receive signal converted into the form of I/Q baseband. For example, the instantaneous frequency $\omega_B$, i.e., $\phi'(t)$ can be obtained by calculating the correlation of the first receive signals converted I/Q baseband signals at time t and at time t+T as shown in equation 9.

$$\phi'(t) = \omega_B(t) = \frac{\arg\langle x_1(t) \cdot x_1^*(t+T) \rangle}{T} \quad \text{(Equation 9)}$$

In equation 9, 'T' denotes a sampling period.

Referring to equation 8, if $\omega_0 \gg \omega_B(t)$, the delay $\tau$ can be computed approximately as shown in equation 10.

$$\tau = \frac{\Delta\Phi}{\omega_0} \quad \text{(Equation 10)}$$

An error of the delay will arise, if the denominator of the equation 10 is fixed as the center frequency $\omega_0$ of the transmitting signal, since the first and the second receive signals have wide bandwidths and the frequencies thereof vary with depth of the tissues in the target object. The error can be reduced by using components of the instantaneous frequency $\omega_B$ of the first or the second receive signal converted into I/Q baseband signal.

When the stress is applied to the target object, the shape of the second receive signal changes with respect to the first receive signal. The displacement of the target object increases as the depth of the tissue in the target object becomes deeper, because the phase difference of the first and the second receive increases in proportional to the depth of the tissue. Therefore, decorrelation of the first and the second receive signals and the error of the delay are relatively large in a deep region.

The decorrelation and the error of the deep region can be reduced by determining the delay of the second receive signal in the deep region with use of the delay of the second receive region in a shallow region. To this end, a delay amount of the second receive signal in the shallow region is estimated, one of the first and the second receive signals is shifted as much as the estimated delay amount such that the delay decreases. Then the delay between the two receive signals in the deep region is computed. Consequently, the delay of the second signal in the deep region can be obtained by a sum of the estimated delay amount and the computed delay, in which the shift is reflected. Details of these processes will be explained with reference to FIGS. 3a and 3b.

Figure 3A:
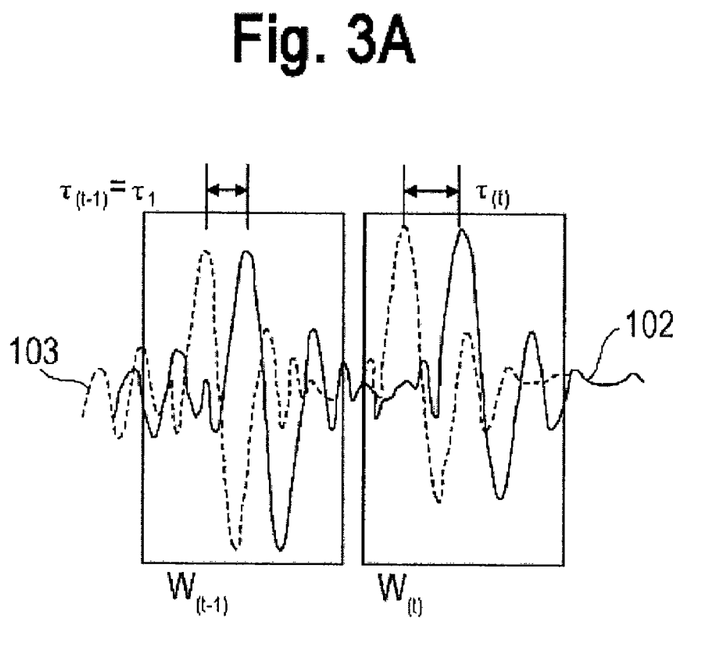
FIG. 3a shows the first and the second receive signals in adjacent two windows.
Figure 3B:
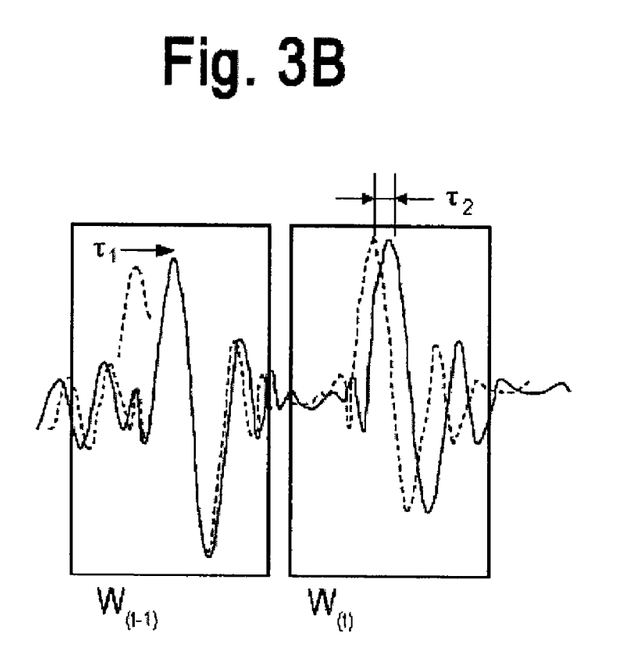
FIG. 3b shows the first receive signal and the second receive signal shifted as much as an estimated delay amount.

In an embodiment of the present invention, the first and second receive signals are divided into a plurality of windows according to the depth of the tissue in the target object or lapse of time. FIGS. 3a and 3b show a windows w(t−1) and w(t) dividing the first receive signal 102 and the second receive signal 103. The window w(t−1) and window w(t) correspond to the shallow region and the deep region, respectively.

As can be seen from the comparison of the first and the second receive signals in the two windows w(t−1) and window w(t), the phase difference and the delay increase when the depth becomes deeper, i.e., when the lapse of time becomes longer. If the two windows are adjacent to each other, the phase difference and the delay between the first and the second receive signals in the two windows are not so great, and therefore the aliasing can be effectively prevented, which otherwise occurs when the phase difference is greater than $\pi$.

If the delay between the first and the second receive signals in the window w(t−1) is $\tau(t-1) = \tau_1$, the estimated delay amount of the second signals is determined as $\tau_1$ in window w(t) adjacent to the window w(t−1).

As shown in FIG. 3b, when the second receive signal is shifted as much as the estimated delay amount $\tau_1$ in accordance with a linear interpolation method, the phase difference between the first receive signal and the shifted second receive signal in the window w(t−1) becomes zero since the two signals are completely overlapped by the shift.

After the shift, the delay $\tau_2$ of the second receive signals in the window w(t) is computed. The computed delay $\tau_2$ in the window w(t) is smaller than the estimated delay amount $\tau_1$. Consequently, the correlation between the first and the second receive signals in the window w(t) increases, and therefore noise and the aliasing decrease owing to the reduced delay.

Since the computed delay $\tau_2$ of the second receive signal in the window w(t) reflects the shift of the second receive signal as much as the estimated delay amount $\tau_1$, the delay $\tau(t)$ of the second receive signal in the window w(t) can be determined by taking the estimated delay amount $\tau_1$ into account, and thus the delay in the window w(t−1) is determined as $\tau(t) = \tau_1 + \tau_2$.

An ultrasound elasticity image, i.e., the strain image is formed in consideration of the delay $\tau_2$ which reflects the estimated delay amount $\tau_1$ in the window w(t−1) corresponding to the relatively shallow region. Therefore, the error associated with the decorrelation of the first and the second receive signals in the deep region can be decreased. In other words, the strain image is formed by reflecting the estimated delay amount $\tau_1$ having relatively low decorrelation and the delay $\tau_2$ determined based on the estimated displacement $\tau_1$, instead of using the delay $\tau(t)$ of the second receive signal as it is, which has relatively high decorrelation.

A displacement $X_{int\_pl}(t)$ of the tissue due to the stress in window w(t) can be expressed as equation 11 below.

$$x_{intpl}(t) = \left(\frac{\tau_1}{T} - \left\lfloor\frac{\tau_1}{T}\right\rfloor\right)x_1(t + \lceil\tau_1/T\rceil T) + \left(\left\lceil\frac{\tau_1}{T}\right\rceil - \frac{\tau_1}{T}\right)x_1(t + \lfloor\tau_1/T\rfloor T) \quad \text{(Equation 11)}$$

In equation 11, "$\lceil\cdot\rceil$" and "$\lfloor\cdot\rfloor$" denote constants close to $+\infty$ and $-\infty$, respectively.

The delay $\tau(t)$ of the second receive signal at time 't' in window w(t) can be obtained based on the estimated delay amount $\tau_1 = \tau(t-1)$ and the correlation of the displacement $x_{int\_pl}(t)$ and the second receive signal $x_2(t)$, as expressed in equation 12.

$$\tau(t) = \tau(t-1) + \frac{\arg\langle x_{intp} \cdot x_2^*\rangle}{\omega_0 + \omega_B(t)} \quad \text{(Equation 12)}$$

In equation 12, the second term is the delay $\tau_2$ of the second receive signal in the window (t) with respect to the estimated delay amount $\tau_1$. As shown in the equation 12, the delay $\tau(t)$ in the window w(t) is determined in consideration of the instantaneous frequency $\omega_B(t)$, and therefore the errors due to the fixed center frequency $\omega_0$ may be decreased. In other words, the error, associated with using the delay $\tau(t)$ as it is, can be reduced, because the delay $\tau(t)$ is determined in consideration of the delay $\tau_1 = \tau(t-1)$ in the window w(t−1) and the delay $\tau_2$ in the window w(t) between the shifted signal and the non-shifted signal, which is expressed as the second term in the equation 12. Therefore, the influence caused by the decorrelation can be reduced.

Figure 4:
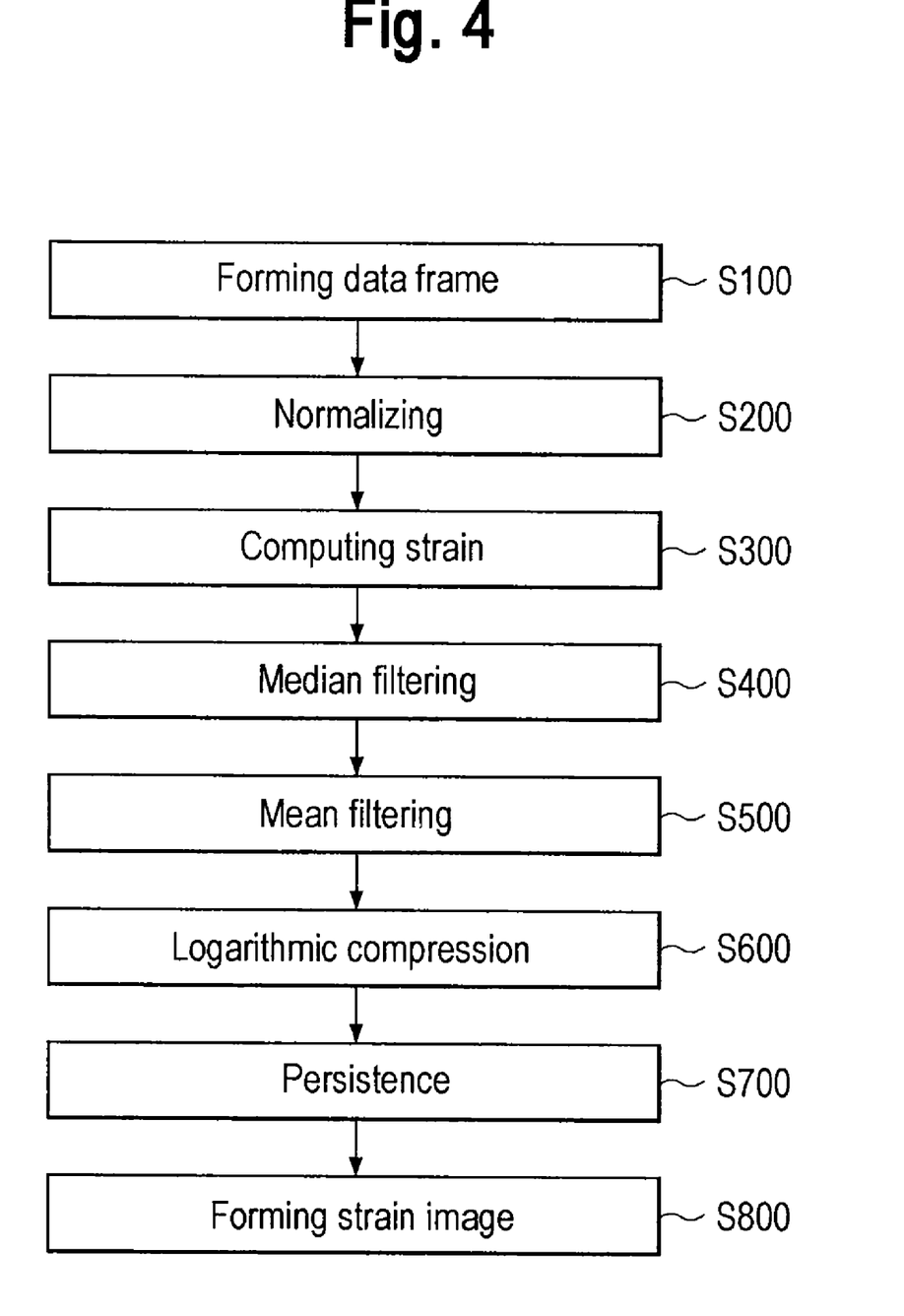
FIG. 4 is a flow chart showing a method of forming an ultrasound elasticity image according to the present invention.

With reference to FIG. 4, a method of forming ultrasound elasticity images will be described.

Referring to FIG. 4, the first and the second receive signals in the RF form are demodulated and converted into the I/Q baseband signals, and a data frame comprising the I/Q baseband signals is formed (S100). The I/Q baseband signals in the data frame are normalized (S200), strain is computed with the I/Q baseband signals (S300), and a median filtering, a mean filtering, a logarithmic compression and persistence are performed one after another (S400, S500, S600, S700), and thereafter stain images are formed (S800).

The computation of strain by decreasing the decorrelation of the receive signals will be described in detail.

The data frame is divided into a plurality of windows according to the depth of the tissues in the target object or the lapse of time. A target window for decreasing the decorrelation and a reference window adjacent to the target window are selected among the plurality of windows. The target window and the reference window can be windows w(t) and w(t−1) of FIGS. 3a and 3b, respectively.

A delay amount is estimated in the reference window. One of the first and the second receive signals in the target window is selected and shifted as much as the estimated delay amount. Afterwards, the instantaneous frequency and the delay are computed by using the correlation method. Thereafter, the strain is computed on the basis of the delay.

Figure 5:
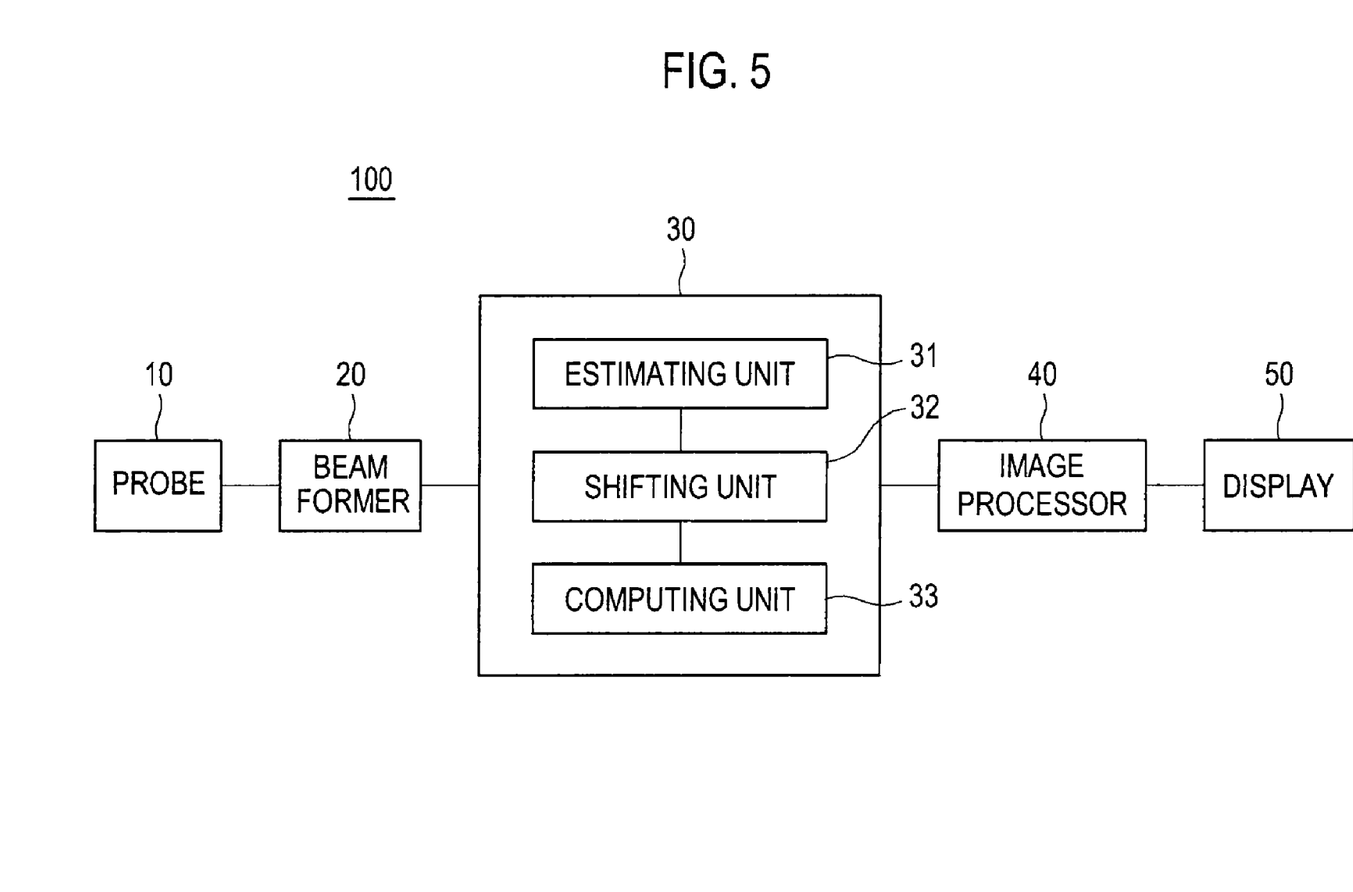
FIG. 5 shows a block diagram of an ultrasound system in accordance with an embodiment of the present invention.

Referring to FIG. 5, the probe 10 of the ultrasound system 100 in accordance with one embodiment may transmit/receive ultrasound signals to/from a target object. The beam former 20 may form receive signals in an RF form with the ultrasound signal received from the target object. The receive signals may include a first receive signal obtained without applying stress to the target object and a second receive signal obtained with applying the stress. One of the first and second receive signals may be delayed with respect to the other. For example, when the stress is applied, the tissues in the target object move along the direction of the stress so that the second receive signal is delayed compared to the first receive signal. As shown in FIGS. 3a and 3b, the first and second receive signals may be divided into a plurality of windows according to depths in the target object or the lapse of time.

The signal processor 30 may compute instantaneous frequency varying with the depths in the target object and form a strain with the first and second receive signals by using the instantaneous frequency.

The image processor 40 may form strain image data based on the strain. Further, the display 50 may display the strain image.

Figure 6:
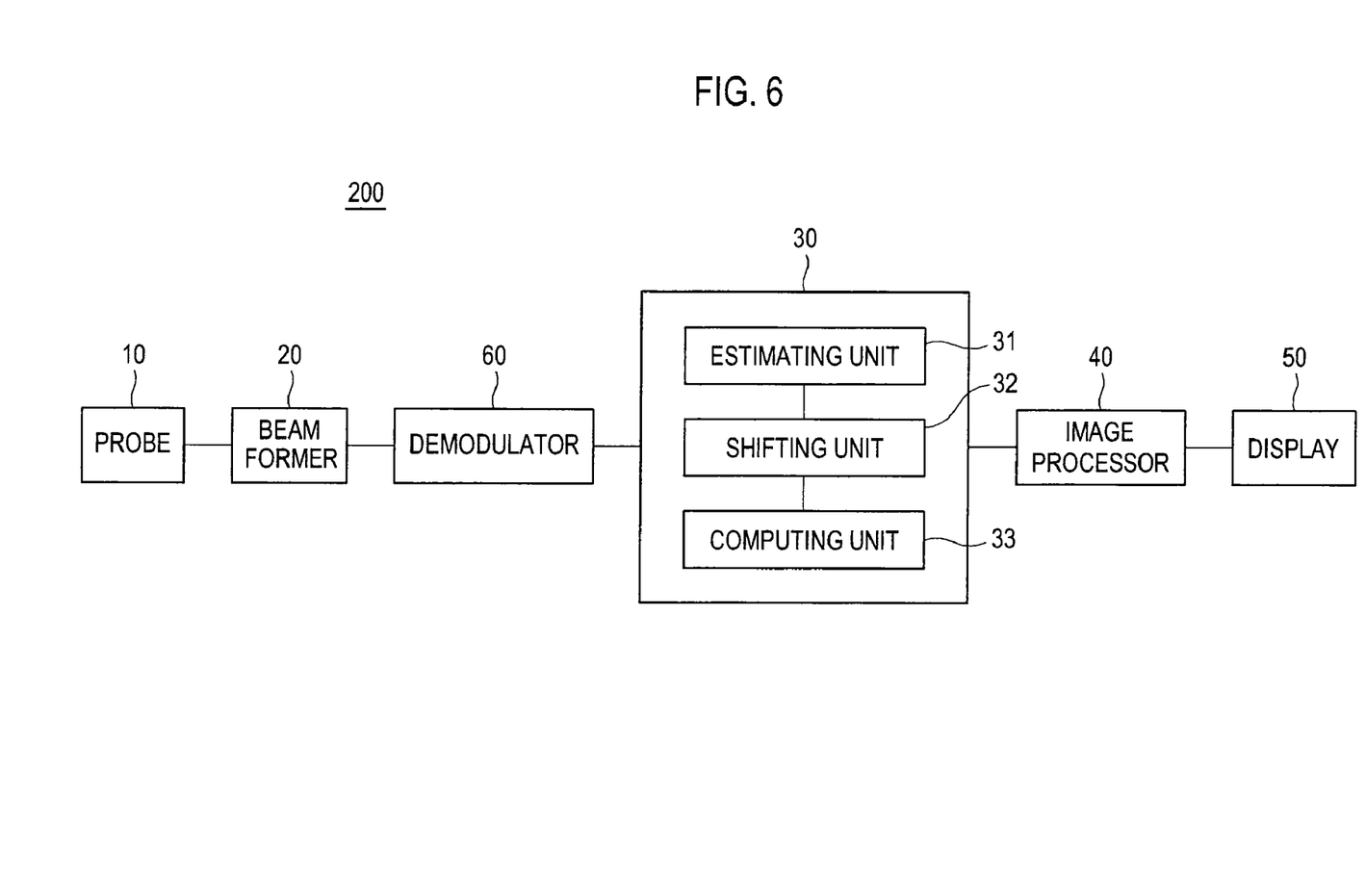
FIG. 6 shows a block diagram of an ultrasound system in accordance with another embodiment of the present invention.

Referring to FIG. 6, the beam former 20 of the ultrasound system 200 in accordance with another embodiment 200 may form the first and receive signals in an RF form. The ultrasound system may further include a demodulator 60 configured to demodulate the first and second receive signals in the RF. By demodulating, the first and second receive signals can be converted into I/Q baseband signals, as shown in equations 3 and 4.

The signal processor 30 of the ultrasound system 100 or 200 may form a strain with the first and second receive signals. An estimating unit 31 of the signal processor may estimate a first delay amount $\tau_1$. The first delay amount $\tau_1$ may be a delay amount of the second receive signal with respect to the first receive signal in the reference window w(t−1). A shifting unit 32 may shift one of the first and second signal as much as the first delay amount $\tau_1$ in the target window w(t) deeper than the reference window w(t−1). A computing unit 33 may compute a first correlation of the first or second receive signal at a different time in a manner of the autocorrelation, compute instantaneous frequency at target window w(t) by using the first correlation as shown in equation 9, compute displacement caused by the stress in target window w(t) in consideration of the first delay amount $\tau_1$ as shown in equation 11, compute a second correlation of the displacement and the second receive signal, compute a second delay amount $\tau_2$ with respect to the first delay amount $\tau_1$ in the target window w(t) by using the instantaneous frequency and the second correlation as shown in the second term of equation 12, compute delay of the second receive signal with respect to the first receive signal in the target window w(t) by using the first delay amount $\tau_1$ and the second delay amount $\tau_2$ according to equation 12, and compute strain (distortion ratio) with the first and second receive signals based on the second delay amount.

In the ultrasound system 100 or 200, the image processor 40 may form strain image data based on the strain. The display 50 may display the strain image.

According to an example embodiment of the present invention, an ultrasound system may be provided to form strain images. The system may include a probe, a beam former, a signal processor, an image processor and a display. The probe may transmit/receive ultrasound signals to/from a target object. The beam former may form receive signals. The receive signals may include a first receive signal and a second receive signal, wherein one of the first and second receive signals may be delayed with respect to the other, and wherein the first and second receive signals may be divided into a plurality of windows according to depths in the target object. The first receive signal may be obtained without applying stress to the target object and the second receive signal may be obtained with applying stress to the target object. The signal processor may compute instantaneous frequency varying with the depths in the target object and form strain with the first and second receive signals by using the instantaneous frequency. The image processor may form strain image data based on the strain. The display may display the strain image.

The signal processor may include an estimating unit configured to estimate a first delay amount in a reference window, a shifting unit configured to shift one of the first and second signal as much as the first delay amount in a target window deeper than the reference window, and a computing unit configured to compute. The computing unit may compute a first correlation of the first or second receive signal at a different time in a manner of the autocorrelation, instantaneous frequency at the target window by using the first correlation, displacement caused by the stress in the target window in consideration of the first delay amount, a second correlation of the displacement and the second receive signal, a second delay amount with respect to the first delay amount in the target window by using the instantaneous frequency and the second correlation, a delay of the second receive signal with respect to the first receive signal in the target window by using the first delay amount and the second delay amount, and strain with the first and second receive signals based on the second delay amount.

According to another example of the present invention, the beam former may form the receive signals in an RF form. The ultrasound system may further comprise a demodulator configured to demodulate the first and second receive signals of the RF form into I/Q baseband signals.

As explained above, the instantaneous frequency changes depend on the depth of the tissues, therefore it can reduce errors which occurs during the conversion of the phase value into the time value. Further, the shift of the receive signal increases the correlation, which results in reduction of noises and the aliasing of phase.

While the present invention has been shown and described with respect to a preferred embodiment, those skilled in the art will recognize that various changes and modifications may be made without departing from the spirit and scope of the invention as defined in the appended claims.

What is claimed is:

1. An ultrasound system, comprising:
   a probe configured to transmit/receive ultrasound signals to/from a target object;
   a beam former configured to form receive signals, wherein the receive signals include a first receive signal and a second receive signal, one of the first and second receive signals being delayed with respect to the other, and wherein each of the first and second receive signals are divided into a plurality of windows according to depths in the target object;
   a signal processor configured to compute a correlation of one of the first and second receive signals at different times separated by a predetermined sampling period to obtain an instantaneous frequency varying with the depths in the target object and form a strain with the first and second receive signals by using the instantaneous frequency;
   an image processor configured to form strain image data based on the strain; and
   a display configured to display the strain image data.

2. The ultrasound system of claim 1, wherein the first receive signal is obtained without applying stress to the target object and the second receive signal is obtained with applying the stress to the target object.

3. The ultrasound system of claim 1, wherein the signal processor includes:
   an estimating unit configured to estimate a first delay amount in a reference window;
   a shifting unit configured to shift one of the first and second signals as much as the first delay amount in a target window deeper than the reference window; and
   a computing unit configured to compute:
      a first correlation of the first or second receive signal at a different time by the predetermined sampling period in a manner of the autocorrelation;
   the instantaneous frequency at the target window by using the first correlation,
      displacement caused by the stress in the target window in consideration of the first delay amount;
      a second correlation of the displacement and the second receive signal;
      a second delay amount with respect to the first delay amount in the target window by using the instantaneous frequency and the second correlation;
      a delay of the second receive signal with respect to the first receive signal in the target window by using the first delay amount and the second delay amount; and
      strain with the first and second receive signals based on the second delay amount.

4. An ultrasound system, comprising:
   a probe configured to transmit/receive ultrasound signals to/from a target object;
   a beam former configured to form receive signals with the ultrasound signal received from the target object, wherein the receive signals include a first receive signal obtained without applying stress to the target object and a second receive signal obtained with applying the stress, one of the first and second receive signals being delayed with respect to the other, and wherein each of the first and second receive signals are divided into a plurality of windows according to depths in the target object;
   a signal processor configured to form a strain with the first and second receive signals, wherein the signal processor includes:
   an estimating unit configured to estimate a first delay amount in a reference window;
   a shifting unit configured to shift one of the first and second signals as much as the first delay amount in a target window deeper than the reference window; and
   a computing unit configured to compute:
      a first correlation of the first or second receive signal at a different time separated by a predetermined sampling period in a manner of the autocorrelation;
      instantaneous frequency at the target window by using the first correlation,
      displacement caused by the stress in the target window in consideration of the first delay amount;
      a second correlation of the displacement and the second receive signal;

a second delay amount with respect to the first delay amount in the target window by using the instantaneous frequency and the second correlation;
a delay of the second receive signal with respect to the first receive signal in the target window by using the first delay amount and the second delay amount; and
strain with the first and second receive signals based on the second delay amount;
an image processor configured to form strain image data based on the strain; and
a display configured to display the strain image data.

5. The ultrasound system of claim 4, wherein the beam former forms the receive signals in an RF form.

6. The ultrasound system of claim 5, further comprising:
a demodulator configured to demodulate the first and second receive signals of the RF form into I/Q baseband signals.

* * * * *